US008901083B2

(12) United States Patent
Tuszynski

(10) Patent No.: US 8,901,083 B2
(45) Date of Patent: Dec. 2, 2014

(54) ADMINISTRATION OF ANGIOCIDIN FOR THE TREATMENT OF LEUKEMIA

(75) Inventor: George P. Tuszynski, Pittsgrove, NJ (US)

(73) Assignee: Temple University, Philadelphia, PA (US)

( * ) Notice: Subject to any disclaimer, the term of this patent is extended or adjusted under 35 U.S.C. 154(b) by 470 days.

(21) Appl. No.: 13/130,898

(22) PCT Filed: Nov. 20, 2009

(86) PCT No.: PCT/US2009/065301
§ 371 (c)(1),
(2), (4) Date: Jul. 28, 2011

(87) PCT Pub. No.: WO2010/065342
PCT Pub. Date: Jun. 10, 2010

(65) Prior Publication Data
US 2011/0288021 A1 Nov. 24, 2011

Related U.S. Application Data

(60) Provisional application No. 61/117,745, filed on Nov. 25, 2008, provisional application No. 61/145,836, filed on Jan. 20, 2009.

(51) Int. Cl.
*A61K 38/00* (2006.01)
*A61P 35/02* (2006.01)
*C07K 14/00* (2006.01)
*A61K 38/17* (2006.01)

(52) U.S. Cl.
CPC .................................. *A61K 38/1709* (2013.01)
USPC .......................................... 514/19.6; 530/350

(58) Field of Classification Search
None
See application file for complete search history.

(56) References Cited

U.S. PATENT DOCUMENTS

| 4,746,508 A | 5/1988 | Carey |
| 2003/0180295 A1* | 9/2003 | Tuszynski et al. ......... 424/143.1 |

FOREIGN PATENT DOCUMENTS

WO 2007100845 A2 9/2007

OTHER PUBLICATIONS

Gaurnier-Hausser et al., The Novel Angiogenic Inhibitor, Angiocidin, Induces Differentiation of Monocytes to Macrophages, Cancer Research, vol. 68, No. 14, Jul. 15, 2008, pp. 5905-5914.
Liebig et al, "Angiocidin Inhibitory Peptides Decrease Tumor Burden in a Murine Colon Cancer Model", Journal of Surgical Research, vol. 142, No. 2, Sep. 20, 2007, pp. 320-326.
Sabherwal et al., "Integrin Alpha2beta1 mediates the anti-angiogenic and anti-tumor activities of angiocidin, a novel tumor-associated protein", Experimental Cell Research, vol. 312, No. 13, Aug. 1, 2006, pp. 2443-2453.
Gaurnier-Hausser et al., "The Immunomodulatory Role of Angiocidin, a Novel Angiogenesis Inhibitor", Current Pharmaceutical Design, vol. 15. No. 17, Jan. 1, 2009, pp. 1937-1948.
Kremlev et al., "Angiocidin promotes pro-inflammatory cytokine production and antigen presentation in multiple sclerosis", Journal of Neuroimmunology, vol. 194, No. 1-2, Jan. 22, 2008, pp. 132-142.
Dimitrov et al., "Endothelial apoptotic activity of angiocidin is dependent on its polyubiquitin binding activity", British Journal of Cancer, vol. 93, No. 6, Sep. 19, 2005, pp. 662-669.
Zhou et al., "Cloning and Characterization of Angiocidin, a Tumor Cell Binding Protein for Thrombospondin-1", Journal of Cellular Biochemistry, vol. 92, No. 1, May 1, 2004, pp. 125-146.
International Search Report dated May 3, 2010.
Written Opinion of the International Search Authority dated May 3, 2010.
Andreesen et al., "Adoptive Immunotherapy of Cancer Using Monocyte-Derived Macrophages: Rationale, Current Status, and Perspectives", Journal of Leukocyte Biology, vol. 64, Oct. 1998, pp. 419-426.
Bingle et al., "The Role of Tumour-Associated Macrophages in Tumour Progression: Implications for New Anticancer Therapies", Journal of Pathology, vol. 196, 2002, pp. 254-265.
Dong et al., "Macrophage-Derived Metalloelastase Is Responsible for the Generation of Angiostatin in Lewis Lung Carcinoma", Cell Press, vol. 88, Mar. 21, 1997, pp. 801-810.
Fang et al., "A Tumorigenic Subpopulation With Stem Cell Properties in Melanomas", Cancer Res, vol. 65, No. 20, Oct. 15, 2005, pp. 9328-9337.
Mantovani et al., "The Origin and function of Tumor-Associated Macrohages", Immonology Today, vol. 13, No. 7, 1992, pp. 265-270.
Mantovani et al., "Macrophage Polarization: Tumor-Assocated Macrophages As a Paradigm for Polarized M2 Mononuclear Phagocytes, Trends in Immunology", vol. 23, No. 11, Nov. 2002, pp. 549-555.
Nesbit et al., "Low-Level Monocyte Chemoattractant Protein-1 Stimulation of Monocytes Leads to Tumor Formation in Nontumorigenic Melanoma Cells1", The Journal of Immunology, vol. 166, 2001, p. 6483-6490.
Poon et al., "Clinical Significance of Thrombospondin 1 Expression in Hepatocellular Carcinoma", Clinical Cancer Research, vol. 10, Jun. 15, 2004, pp. 4150-4157.
Reyes et al., "Effects of Mycoplasma Fermentans Incognitus on Differentiation of THP-1 Cells", Infection and Immunity, vol. 67, No. 7, Jul. 1999, pp. 3188-3192.
Robb et al., "T Cell Growth Factor Receptors", J. Exp. Med, vol. 154, Nov. 1981, pp. 1455-1474.
Yokoyama et al., "Synergy Between Angiostatin and Endostatin: Inhibition of Ovarian Cancer Growth1", Cancer Research, vol. 60, Apr. 15, 2000, pp. 2190-2196.

* cited by examiner

*Primary Examiner* — Elly-Gerald Stoica
(74) *Attorney, Agent, or Firm* — Riverside Law LLP

(57) ABSTRACT

Methods are presented for the therapeutic administration of angiocidin in the treatment of cancers such as glioma, breast cancer, and leukemia. Methods are also presented for inducing growth arrest and/or apoptosis of tumor cells, as well as inducing differentiation of tumor cells to inhibit tumorigenicity and to confer a non-tumor or healthy phenotype.

13 Claims, 13 Drawing Sheets

Fig. 12A
Fig. 12B
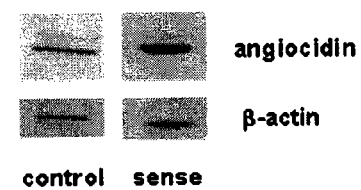
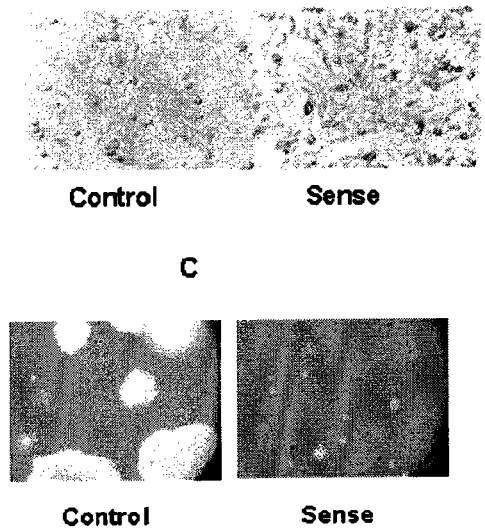
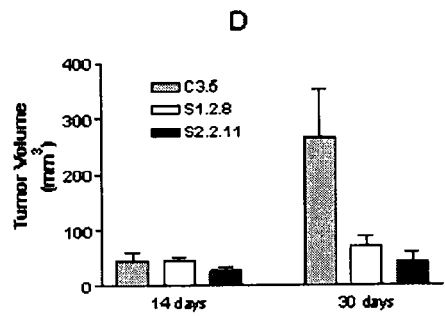
Fig. 12C
Fig. 12D

ADMINISTRATION OF ANGIOCIDIN FOR THE TREATMENT OF LEUKEMIA

CROSS REFERENCE TO RELATED APPLICATIONS

This application is a U.S. national stage application of the PCT International Application No. PCT/US2009/065301, filed Nov. 20, 2009, which claims priority to U.S. Provisional Application Nos. 61/145,836, filed Jan. 20, 2009, and 61/117,745, filed Nov. 25, 2008. Each of these applications is incorporated by reference herein, in its entirety and for all purposes.

STATEMENT REGARDING FEDERALLY SPONSORED RESEARCH

This invention was made with government support under R01 CA88931 awarded by the National Institutes of Health. The government has certain rights in the invention.

BACKGROUND OF THE INVENTION

Various publications, including patents, published applications, technical articles and scholarly articles are cited throughout the specification. Each of these cited publications is incorporated by reference herein, in its entirety.

Solid human tumors are often infiltrated by host immune cells, which can have a diverse effect on tumor progression. Among other cell types, macrophages are known to be a major component in the leukocyte infiltrate in tumors. These tumor-associated macrophages, (TAMs), have a complex dual function in their interactions with neoplastic cells (Mantovani, et al., *Trends Immunol.* 23: 549-555, 2002). First, TAMs stimulate cell destruction through antigen presentation to T-cells, which induces cytotoxic T-cells to kill tumor cells bearing the presented antigen. In contrast, TAMs also promote cell proliferation and angiogenesis, thus affecting tissue growth.

These contradictory effects can be explained in terms of the "macrophage balance hypothesis," which asserts that the outcome of the interaction between macrophages and neoplastic cells depends on the number of macrophages recruited to the tumor microenvironment and their state of activation (Mantovani, et al., *Immunol. Today* 13: 265-270, 1992; Bingle, et al., *J. Pathol.* 196: 254-265, 2002; Nesbit, et al., *J. Immunol.* 166: 6483-6490). Nesbit, et al. have shown that, in a mouse model, high levels of monocyte chemoattractant protein-1 (MCP-1) secreted by melanoma cells is associated with massive monocyte/macrophage infiltration into the tumor mass, leading to destruction of the tumor within a few days. However, low levels of secreted MCP-1 stimulated angiogenesis and tumor growth. Furthermore, ex vivo-grown cytotoxic macrophages that recognize and destroy tumor cells, but not normal cells, are effective in murine models of metastasizing tumors. (Andreesen, et al., *J. Leukocyte Biol.* 64: 419-426, 1998). Accordingly, immunomodulation, in particular regulating macrophage activity, has potential as a therapeutic strategy for the treatment of tumors, secondary metastasis, and other disorders.

Angiocidin is a protein, originally isolated from lung carcinoma, that is overexpressed in many tumor systems (Zhou et al., *J. Cell. Biochem.* 92: 125-146, 2004; Poon, et al., *Clin. Cancer Res.* 12: 4150-4157, 2004). Angiocidin is a receptor for thrombospondin-1 and is a potent inhibitor of angiogenesis and tumor cell proliferation (U.S. 2003/0180295; Zhou et al., *J. Cell. Biochem.* 92: 125-146, 2004). These functions of angiocidin are mediated by α2β1 integrin (Sabherwal, et al., *Exp. Cell Res.* 312: 443-453, 2006). In addition, angiocidin has important immunomodulatory effects on monocytes that can affect the course of disease.

SUMMARY OF THE INVENTION

The invention features methods for treating tumors such as glioma, breast cancer, and leukemia. The methods generally comprise administering to a subject having a glioma, breast cancer, or leukemia an amount of angiocidin effective to treat the glioma, breast cancer, or leukemia. The angiocidin can be administered to the subject as a composition comprising a pharmaceutically acceptable carrier. The amount of angiocidin administered to the subject can vary according to the type of tumor, or other variables, but generally will be a dose of about 0.001 to 10 mg/kg body weight of the subject.

In some aspects, the methods further comprise administering to the subject an effective amount of a growth factor such as fibroblast growth factor-2 (FGF-2), nerve growth factor (NGF), brain-derived neural factor (BDNF), neurotropin-3 (NT-3), epidermal growth factor (EGF), or stem cell growth factor (SCF). The angiocidin can complex with the growth factor. In some aspects, the angiocidin-growth factor complex can induce growth arrest of the tumor cells, such as the glioma, breast cancer, or leukemia cells. In some aspects, the angiocidin-growth factor complex can promote healthy stem cell differentiation at or proximal to the site of the glioma or breast cancer, or in the blood or the bone marrow.

The invention also features methods for arresting growth of tumor cells. The methods generally comprise contacting the tumor cell with an amount of angiocidin effective to arrest growth of the tumor cell. In some aspects, subsequent to or concomitant with the growth arrest, the tumor cell undergoes apoptosis. The methods are preferably used to arrest the growth of glioma cells, breast cancer cells, leukemia cells, and melanoma cells. In some aspects, the angiocidin can be complexed with a growth factor such as fibroblast growth factor-2 or nerve growth factor.

The invention also features methods for inducing differentiation of leukemia cells. The methods generally comprise contacting the leukemia cell with an amount of angiocidin effective to induce differentiation of the leukemia cell. Leukemia cell differentiation preferably inhibits the tumorigenicity of the leukemia cell. In some aspects, induced leukemia cell differentiation confers a non-cancerous phenotype.

The invention also features methods for treating tumors that express a growth factor receptor. The methods generally comprise administering to a subject having a tumor that expresses a receptor for fibroblast growth factor-2, nerve growth factor, brain-derived neural factor, neurotropin-3, epidermal growth factor, or stem cell growth factor an amount of angiocidin effective to treat the tumor expressing a receptor for fibroblast growth factor-2, nerve growth factor, brain-derived neural factor, neurotropin-3, epidermal growth factor, or stem cell growth factor. The angiocidin can be administered to the subject as a composition comprising a pharmaceutically acceptable carrier. The amount of angiocidin administered to the subject can vary according to the type of tumor, or other variables, but generally will be a dose of about 0.001 to 10 mg/kg body weight of the subject. The tumor expressing a receptor for such growth factors can be, for example, glioma, breast cancer, leukemia, or melanoma among others.

BRIEF DESCRIPTION OF THE DRAWINGS

FIG. 12 shows that MDA-MB-231 human breast tumor cells transfected with angiocidin to over-express angiocidin formed smaller colonies in soft agar and developed smaller tumors when injected subcutaneously into athymic mice.

DETAILED DESCRIPTION OF THE INVENTION

Figure 1:
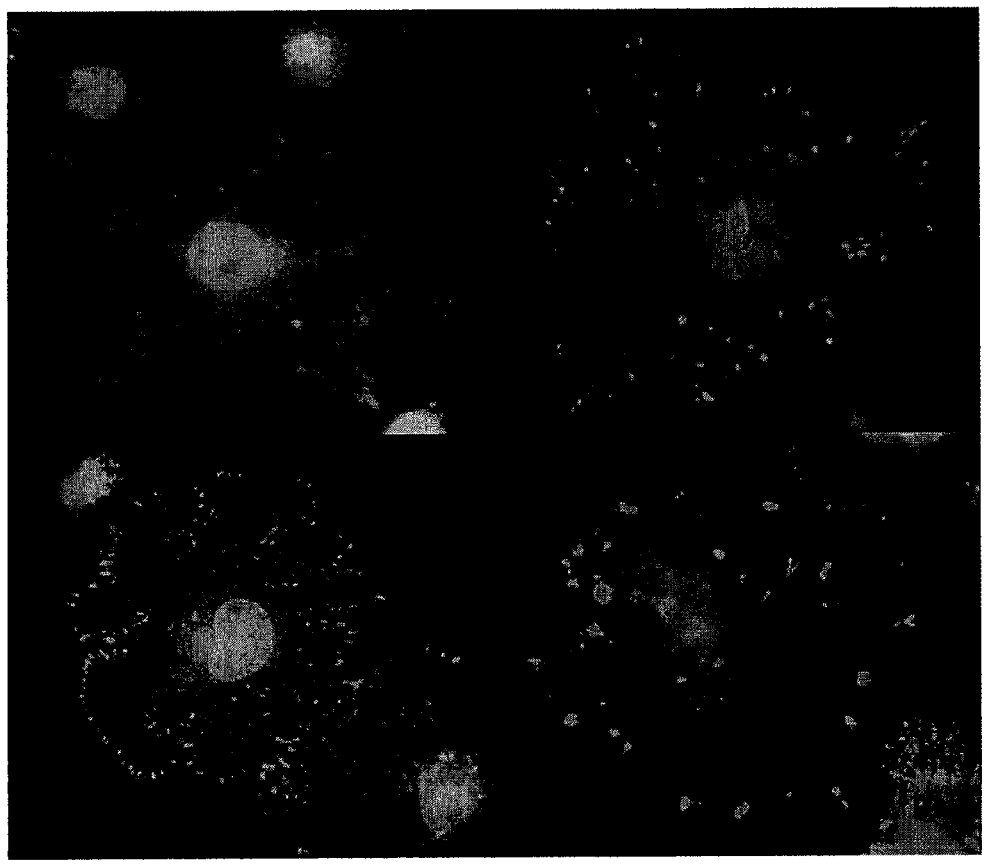
FIG. 1 shows a fluorescence micrograph showing the macrophage-like morphology and formation of focal adhesions by THP-1 cells treated with angiocidin. Cells were reacted with an anti-vinculin antibody and DAPI.

As used in this specification and the appended claims, the singular forms "a", "an" and "the" include plural unless the content clearly dictates otherwise. Thus, for example, reference to "a cell" includes a combination of two or more cells, and the like.

"Effective amount" or "therapeutically effective amount" are used interchangeably herein, and refer to an amount of angiocidin, a growth factor, or composition, including those as described herein, effective to achieve a particular biological result such as, but not limited to, biological results disclosed, described, or exemplified herein. Such results may include, but are not limited to, the treatment of tumors in a subject, as determined by any means suitable in the art.

Except when noted, "subject" or "patient" are used interchangeably and refer to mammals such as humans and non-human primates, as well as companion, farm, or experimental animals such as rabbits, dogs, cats, rats, mice, horses, cows, pigs, and the like. Humans are most preferred.

Recent studies have shown that angiocidin stimulates important cellular immune system responses. Angiocidin activates monocytes, stimulating the production of proinflammatory cytokines and chemokines and stimulating antigen presentation to T-cells, which leads to the formation of cytotoxic T-cells. Furthermore, angiocidin induces the differentiation of monocytes to macrophages. Because of these activities, angiocidin has previously unknown therapeutic value for the treatment of a number of disorders that are regulated, at least in part, by the immune system, including tumor cell metastasis, leukemia, wound healing, skin damage, and autoimmune disorders such as multiple sclerosis.

The ability of cancer cells to metastasize to distant sites in the body is responsible for the majority of cancer-related deaths. The surgical removal of a primary tumor can stimulate metastasis and secondary tumor formation, suggesting that primary tumors secrete factors that inhibit secondary metastases. Two such factors, endostatin and angiostatin, have been described (Dong, et al., *Cell* 88: 801-810, 1997; Yokoyama, et al., *Cancer Research* 60: 2190-2196, 2000). Angiocidin appears to be another inhibitory factor of tumor origin that can prevent or treat secondary metastasis by stimulating macrophage differentiation and recruiting cytotoxic T-cells to the metastatic site for tumor cell destruction. As a result, secondary tumor development is prevented. Accordingly, in one embodiment of the invention, a composition comprising angiocidin and a pharmaceutically acceptable carrier is administered to a subject in need thereof to suppress or prevent metastasis. Angiocidin can also be administered directly to the surgical site following removal of a primary tumor. Particular tumor tissue types that could be treated in this manner include, but are not limited to, breast, colon, lung, prostate, skin, oral, nasal, esophageal, stomach, liver, pancreas, glioma, head, neck, ovarian and uterine.

As described in detail in Examples 2 and 3, angiocidin activates monocytes and, unexpectedly, induces the differentiation of monocytes to macrophages. Accordingly, in another embodiment of the invention, angiocidin is administered to a subject in need thereof for the treatment of leukemia, which is characterized by the uncontrolled proliferation of leukemic blast cells. Angiocidin induces leukemic cells to differentiate and cease proliferation, thereby correcting the malignant phenotype. This "differentiation therapy" provides a method to manage the disease without debilitating cytotoxic chemotherapy. Similarly, Example 7 demonstrates that angiocidin inhibits the proliferation of stem cells that give rise to melanoma.

In another embodiment, angiocidin is administered to develop and stimulate antigen-presenting macrophages to recruit T-cells to sites of infection. Angiocidin stimulates these T-cells to produce substances, e.g., IL-2 and IL-12, that lyse tumor and foreign cells and raise an immune response against the infective organism. Thus, angiocidin-induced macrophage differentiation and stimulation can be used to treat and prevent viral, bacterial, and protozoal infections. These may include, but are not limited to, herpes simplex virus I and II infections, varicella-zoster virus/Ellen, bovine papilloma virus, and human immunodeficiency virus, hepatitis B and C, influenza, and tuberculosis.

Blastomere-like stem cells (BLSC), totipotent stem cells found in human peripheral blood, will also differentiate in response to angiocidin (Example 6). BLSC were developed by Moraga Biotechnology Corp., Los Angeles, Calif., and are described further in WO/2007/100845. As totipotent cells, BLSC have the ability to differentiate into most mammalian cell types. These native (i.e., not tumor-derived) stem cells are not cancerous when implanted into animals, but can incorporate into all tissues undergoing repair and will proliferate until stimulated by microevironmental cues from cells of a specific tissue to differentiate into that particular cell type. BLSC are capable of generating tissue derived from all three germ layer lineages, including germ cells, in response to a combination of general and specific differentiation signals. These and other characteristics of BLSC are discussed in moragabiotech.com/techblscs.htm. These results indicate that angiocidin has in vitro and in vivo uses as a general induction agent in tissue regeneration, neurogenesis, wound healing or tissue repair. Additionally, angiocidin has applications in cosmetics for neocollagenesis and skin rejuvenation.

The invention provides methods for treating tumors that express a receptor for fibroblast growth factor-2, nerve growth factor, brain-derived neural factor, neurotropin-3, epidermal growth factor, or stem cell growth factor. The methods generally comprise administering to a subject having a tumor that expresses a receptor for fibroblast growth factor-2, nerve growth factor, brain-derived neural factor, neurotropin-3, epidermal growth factor, or stem cell growth factor an amount of angiocidin effective to treat the tumor expressing a receptor for fibroblast growth factor-2, nerve growth factor, brain-derived neural factor, neurotropin-3, epidermal growth factor, or stem cell growth factor. The angiocidin can be administered to the subject as a composition comprising a pharmaceutically acceptable carrier. The amount of angiocidin administered to the subject can vary according to the type of tumor, or other variables, but generally will be a dose of about 0.001 to 10 mg/kg body weight of the subject. The tumor expressing a receptor for fibroblast growth factor-2, nerve growth factor, brain-derived neural factor, neurotropin-3, epidermal growth factor, or stem cell growth factor can be, for example, glioma, breast cancer, leukemia, or melanoma among others.

The invention provides methods for treating a glioma in a subject. The methods generally comprise administering to the subject an amount of angiocidin effective to treat the glioma. The angiocidin can be administered in a composition comprising angiocidin and a pharmaceutically acceptable carrier. The angiocidin can be administered to the subject in a dose of about 0.001 to 10 mg/kg body weight.

The methods may further comprise administering to the subject an effective amount of a growth factor such as fibroblast growth factor-2 (FGF-2), nerve growth factor (NGF), brain-derived neural factor (BDNF), neurotropin-3 (NT-3), epidermal growth factor (EGF), and stem cell growth factor (SCF), or any other growth factor having a basic isoelectric point. FGF-2 and NGF are most preferred. The growth factors can be administered in the same composition with angiocidin. The growth factors can be administered in a different composition, which comprises the growth factor and a pharmaceutically acceptable carrier. The growth factors can be administered at the same time, in advance of, or after the administration of angiocidin.

In some aspects, the angiocidin complexes with the fibroblast growth factor-2, nerve growth factor, brain-derived neural factor, neurotropin-3, epidermal growth factor, or stem cell growth factor, and the complex induces growth arrest of the glioma cells. In some aspects, the complex promotes healthy stem cell differentiation at or proximal to the site of the glioma.

The invention provides methods for treating breast cancer in a subject. The methods generally comprise administering to the subject an amount of angiocidin effective to treat the breast cancer. The angiocidin can be administered in a composition comprising angiocidin and a pharmaceutically acceptable carrier. The angiocidin can be administered to the subject in a dose of about 0.001 to 10 mg/kg body weight.

The methods may further comprise administering to the subject an effective amount of a growth factor such as fibroblast growth factor-2, nerve growth factor, brain-derived neural factor, neurotropin-3, epidermal growth factor, or stem cell growth factor. The growth factors can be administered in the same composition with angiocidin. The growth factors can be administered in a different composition, which comprises the growth factor and a pharmaceutically acceptable carrier. The growth factors can be administered at the same time, in advance of, or after the administration of angiocidin.

In some aspects, the angiocidin complexes with the fibroblast growth factor-2, nerve growth factor, brain-derived neural factor, neurotropin-3, epidermal growth factor, or stem cell growth factor, and the complex induces growth arrest of the breast cancer cells. In some aspects, the complex promotes healthy stem cell differentiation at or proximal to the site of the breast cancer.

The invention provides methods for treating leukemia in a subject. The methods generally comprise administering to the subject an amount of angiocidin effective to treat the leukemia. The angiocidin can be administered in a composition comprising angiocidin and a pharmaceutically acceptable carrier. The angiocidin can be administered to the subject in a dose of about 0.001 to 10 mg/kg body weight.

The methods may further comprise administering to the subject an effective amount of a growth factor such as fibroblast growth factor-2, nerve growth factor, brain-derived neural factor, neurotropin-3, epidermal growth factor, or stem cell growth factor. The growth factors can be administered in the same composition with angiocidin. The growth factors can be administered in a different composition, which comprises the growth factor and a pharmaceutically acceptable carrier. The growth factors can be administered at the same time, in advance of, or after the administration of angiocidin.

In some aspects, the angiocidin complexes with the fibroblast growth factor-2, nerve growth factor, brain-derived neural factor, neurotropin-3, epidermal growth factor, or stem cell growth factor, and the complex induces growth arrest of the leukemia cells. In some aspects, the complex promotes healthy stem cell differentiation in the blood or in the bone marrow.

The invention also provides methods for arresting the growth of a tumor cell. The methods generally comprise contacting the tumor cell with an amount of angiocidin effective to arrest growth of the tumor cell. In some aspects, the tumor cell will undergo apoptosis subsequent to its exposure to angiocidin, and the apoptosis may begin subsequent to the growth arrest. Angiocidin can be used to arrest the growth of any tumor cell, with glioma cells, breast cancer cells, leukemia cells, and melanoma cells being highly preferred. In some aspects, the angiocidin can be complexed with a growth factor such as fibroblast growth factor-2, nerve growth factor, brain-derived neural factor, neurotropin-3, epidermal growth factor, or stem cell growth factor, or other growth factors with similar structures to these growth factors. It is believed that the angiocidin can potentiate the action of such growth factors. The methods can be carried out in vitro or in vivo.

The invention also provides methods for inducing differentiation of a leukemia cell. The methods generally comprise contacting the leukemia cell with an amount of angiocidin effective to induce differentiation of the leukemia cell. The differentiation of the leukemia cell induces genotypic and phenotypic changes that inhibit, and that are capable of reversing the tumorigenicity of the leukemia cell, for example, making the leukemia cell less cancerous. For example, differentiation of leukemic cells may result in downregulation and expression of the oncogene BCL-2. Cells can also be considered less cancerous if they fail to grow in soft agar and display a less invasive phenotype, or are capable of phagocytosis. In some aspects, the differentiation induces the leukemia cell to confer a non-cancerous phenotype, for example, a phenotype characterized by a cell capable of anchorage-dependent growth with a well-defined cytoskeleton. It is believed that angiocidin may induce leukemic cells to lose their potential to initiate a tumor when engrafted into an immunocompromised host. It is believed that the differentiation of a leukemia cell by angiocidin can be enhanced by complexing the angiocidin with a growth factor such as FGF-2, NGF, BDNF, NT-3, EGF, and SCF. The differentiated phenotype in leukemia can be a cell expressing molecules normally expressed by terminally differentiated immune cells such as CD14, a macrophage marker, and molecules that can present antigens to T cells. In addition, such phenotypes include that differentiated cells no longer can self-renew, have a limited lifespan, downregulate oncogenes, cannot metastasize, and are contact inhibited in vitro.

A method of treating a human or other mammal in need thereof with angiocidin comprising administering to the human or other mammal a therapeutically effective dose of angiocidin is also provided. A method for activating or inducing the differentiation of native stem cells comprising administering angiocidin to one or more native stem cells, wherein the stem cells are activated or induced to differentiate into lineages of the three germ layers. A method for inducing differentiation of tumor-derived stem cells comprising administering angiocidin to tumor-derived stem cells in vivo or in vitro, wherein the tumor-derived cancer stem cells are induced to differentiate into cells which lose their ability to hyperproliferate and possess a gene expression profile of terminally differentiated cells, similar to normal cells encompassing the tumor.

Angiocidin may be administered to a subject by any appropriate means, such as enteral, parenteral, transdermal, or by direct injection or application to a diseased site.

Metastasis may be inhibited by applying angiocidin directly to the surgical site following removal of a primary tumor. Dosage is preferably determined by a physician based on the disease to be treated and the physiological status of the subject, however, the dose may range from about 0.001-10 mg/kg body weight, and is preferably at about 0.01 to 1.0 mg/kg body weight. A preferred dosage range for leukemia is about 0.01-0.1 mg/kg. For in vitro use, angiocidin may be applied at about 1-50 µg/mL, preferably at about 5-20 µg/ml.

The effective amount of the angiocidin may be dependent on any number of variables, including without limitation, the species, breed, size, height, weight, age, overall health of the subject, the type of formulation, the mode or manner or administration, the type and/or severity of the particular cancer being treated, the stage of cancer, the extent of metastasis, and the like. The appropriate effective amount can be routinely determined by those of skill in the art using routine optimization techniques and the skilled and informed judgment of the practitioner and other factors evident to those skilled in the art. Preferably, a therapeutically effective dose of the angiocidin will provide therapeutic benefit without causing substantial toxicity to the subject.

Toxicity and therapeutic efficacy of the angiocidin formulations can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents or compositions which exhibit large therapeutic indices are preferred. The data obtained from cell culture assays and animal studies can be used in formulating a range of dosage for use in the subject. The dosage of such agents or compositions lies preferably within a range of circulating concentrations that include the $ED_{50}$ with little or no toxicity. The dosage may vary within this range depending upon the dosage form employed and the route of administration utilized.

For any angiocidin composition used in the methods of the invention, the therapeutically effective dose can be estimated initially from in vitro assays such as cell culture assays. For example, a dose can be formulated in animal models to achieve a circulating plasma concentration range that includes the IC50 as determined in cell culture. Such information can be used to more accurately determine useful doses in a specified subject such as a human. The treating physician can terminate, interrupt, or adjust administration due to toxicity, or to organ dysfunctions, and can adjust treatment as necessary if the clinical response is not adequate in order to improve the response.

In some aspects, the dose of angiocidin administered to the subject can also be measured in terms of total amount of drug administered per day. Treatment can be initiated with smaller dosages that are less than the optimum dose of angiocidin, followed by an increase in dosage over the course of the treatment until the optimum effect under the circumstances is reached. If needed, the total daily dosage may be divided and administered in portions throughout the day.

Angiocidin is preferably administered as a pharmaceutical formulation with one or more carriers and/or excipients that are compatible with both the compounds administered and the subject to whom they are administered. Angiocidin may be administered alone or in combination with another active ingredient. Formulations of angiocidin may be presented in unit-dose or multi-dose forms and may be prepared by any methods known in the pharmaceutical art.

Pharmaceutically acceptable carriers can be either solid or liquid. Non-limiting examples of solid form preparations include powders, tablets, pills, capsules, lozenges, cachets, suppositories, dispersible granules, and the like. A solid carrier can include one or more substances which may also act as diluents, flavoring agents, buffering agents, binders, preservatives, tablet disintegrating agents, or an encapsulating material. Suitable solid carriers include magnesium carbonate, magnesium stearate, talc, sugar, lactose, pectin, dextrin, starch, gelatin, acacia, tragacanth, methylcellulose, sodium carboxymethyl-cellulose, polyethylene glycols, vegetable oils, agar, a low is melting wax, cocoa butter, and the like. Non-limiting examples of liquid form preparations include solutions, suspensions, syrups, slurries, and emulsions. Suitable liquid carriers include any suitable organic or inorganic solvent, for example, water, alcohol, saline solution, buffered saline solution, physiological saline solution, dextrose solution, water propylene glycol solutions, and the like, preferably in sterile form.

Aqueous solutions can be prepared by dissolving the angiocidin and/or growth factor in water and adding suitable colorants, flavors, stabilizing and thickening agents as desired. Aqueous suspensions can also be made by dispersing the finely divided active component in water with viscous material, such as natural or synthetic gums, resins, methylcellulose, sodium carboxymethylcellulose, and other well-known suspending agents.

Solid forms can be prepared according to any means suitable in the art. For example, capsules can be prepared by mixing the active ingredients or composition with a suitable diluent and filling the proper amount of the mixture in capsules. Tablets are prepared by direct compression, by wet granulation, or by dry granulation. Their formulations usually incorporate diluents, binders, lubricants and disintegrators as well as the compound. Non-limiting examples of diluents include various types of starch, cellulose, crystalline cellulose, microcrystalline cellulose, lactose, fructose, sucrose, mannitol, kaolin, calcium phosphate or sulfate, inorganic salts such as sodium chloride and powdered sugar. Powdered cellulose derivatives are also useful. Non-limiting examples of tablet binders include starches, gelatin and sugars such as lactose, fructose, glucose and the like. Natural and synthetic gums are also convenient, including acacia, alginates, methylcellulose, polyvinylpyrrolidone and the like. Polyethylene glycol, ethylcellulose and waxes can also serve as binders.

A lubricant can be used in a tablet formulation to prevent the tablet and punches from sticking in the die. The lubricant can be chosen from such slippery solids as talc, magnesium and calcium stearate, stearic acid and hydrogenated vegetable oils.

Tablet disintegrators are substances which swell when-wetted to break up the tablet and release the compound, and include starches such as corn and potato starches, clays, celluloses, aligns, gums, methylcellulose, agar, bentonite, wood cellulose, powdered natural sponge, cation-exchange resins, alginic acid, guar gum, citrus pulp, carboxymethyl cellulose, and sodium lauryl sulfate. Tablets can be coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established in the art.

Also included are liquid formulations and solid form preparations which are intended to be converted, shortly before use, to liquid form preparations. Such liquid forms include solutions, suspensions, syrups, slurries, and emulsions. Liquid preparations may be prepared by conventional means with pharmaceutically acceptable additives such as suspending agents (e.g., sorbitol syrup, cellulose derivatives or hydrogenated edible fats or oils); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). These preparations may contain, in addition to the active agent, colorants, flavors, stabilizers, buffers, artificial and natural sweeteners, dispersants, thickeners, solubilizing agents, and the like. The compositions may be in powder form for constitution with a suitable vehicle such as sterile water, saline solution, or alcohol, before use.

Permeability enhancers can significantly enhance the permeability of lipophilic and nonlipophilic drugs. Additional forms of chemical enhancers, such as those enhancing lipophilicity, have been developed to improve transport when physically mixed with certain therapeutic agents and provide more predictable absorption. Carriers have also been coupled to pharmaceutical agents to enhance intracellular transport.

Typical permeation enhancers may include bile salts such as sodium cholate, sodium glycocholate, sodium glycodeoxycholate, taurodeoxycholate, sodium deoxycholate, sodium lithocholate chenocholate, chenodeoxycholate, ursocholate, ursodeoxycholate, hydrodeoxycholate, dehydrocholate, glycochenocholate, taurochenocholate, and taurochenodeoxycholate. Other permeation enhancers such as sodium dodecyl sulfate ("SDS"), dimethyl sulfoxide ("DMSO"), sodium lauryl sulfate, salts and other derivatives of saturated and unsaturated fatty acids, surfactants, bile salt analogs, derivatives of bile salts, or such synthetic permeation enhancers as described in U.S. Pat. No. 4,746,508 may be used. It is generally believed that bile salts are good enhancers for hydrophilic drugs and long chain fatty acids, their salts, derivatives, and analogs are more suitable for lipophilic drugs. DMSO, SDS, and medium chain fatty acids (about C-8 to about C-14) their salts, derivatives, and analogs may work for both hydrophilic and lipophilic drugs.

The permeation enhancer concentration within the dissolvable matrix material may be varied depending on the potency of the enhancer and rate of dissolution of the dissolvable matrix. Other criteria for determining the enhancer concentration include the potency of the drug and the desired lag time. The upper limit for enhancer concentration is set by toxic effect to or irritation limits of the mucosal membrane.

The compositions may also include a disintegrating agent. Tablet disintegrators are substances which swell when-wetted to break up the tablet and release the compound, and include starches such as corn and potato starches, clays, celluloses, aligns, gums, methylcellulose, agar, bentonite, wood cellulose, powdered natural sponge, cation-exchange resins, alginic acid, sodium alginate, guar gum, citrus pulp, carboxymethyl cellulose, polyvinylpyrrolidone, and sodium lauryl sulfate. Acrylic type polymers can also advantageously be used as disintegrators, including methacrylic copolymers of type C.

The compositions can be formulated for use in topical administration. Such formulations include, e.g., liquid or gel preparations suitable for penetration through the skin such as creams, liniments, lotions, ointments or pastes, and drops suitable for delivery to the eye, ear or nose.

In some embodiments, the present compositions include creams, drops, liniments, lotions, ointments and pastes are liquid or semi-solid compositions for external application. Such compositions may be prepared by mixing the active ingredient(s) in powdered form, alone or in solution or suspension in an aqueous or non-aqueous fluid with a greasy or non-greasy base. The base may comprise complex hydrocarbons such as glycerol, various forms of paraffin, beeswax; a mucilage; a mineral or edible oil or fatty acids; or a macrogel. Such compositions may additionally comprise suitable surface active agents such as surfactants, and suspending agents such as agar, vegetable gums, cellulose derivatives, and other ingredients such as preservatives, antioxidants, and the like.

The compositions can also be formulated for injection into the subject. For injection, the compositions of the invention can be formulated in aqueous solutions such as water or alcohol, or in physiologically compatible buffers such as Hanks's solution, Ringer's solution, or physiological saline buffer. The solution may contain formulatory agents such as suspending, stabilizing and/or dispersing agents. Injection formulations may also be prepared as solid form preparations which are intended to be converted, shortly before use, to liquid form preparations suitable for injection, for example, by constitution with a suitable vehicle, such as sterile water, saline solution, or alcohol, before use.

The compositions can also be formulated in sustained release vehicles or depot preparations. Such long acting formulations may be administered by implantation (for example subcutaneously or intramuscularly) or by intramuscular injection. Thus, for example, the compositions may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well-known examples of delivery vehicles suitable for use as carriers for hydrophobic drugs.

Administration of the compositions can be by infusion or injection (intravenously, intramuscularly, intracutaneously, subcutaneously, intrathecal, intraduodenally, intraperitoneally, and the like). The compositions can also be administered intranasally, vaginally, rectally, orally, or transdermally. Preferably, the compositions are administered intravenously. Administration can be at the direction of a physician.

For buccal administration, the compositions may take the form of tablets, troche or lozenge formulated in conventional manner. Compositions for oral or buccal administration, may be formulated to give controlled release of the active compound. Such formulations may include one or more sustained-release agents known in the art, such as glyceryl mono-stearate, glyceryl distearate and wax.

Compositions may be applied topically. Such administrations include applying the compositions externally to the epidermis, the mouth cavity, eye, ear and nose. This contrasts with systemic administration achieved by oral, intravenous, intraperitoneal and intramuscular delivery. Compositions for use in topical administration include, e.g., liquid or gel preparations suitable for penetration through the skin such as creams, liniments, lotions, ointments or pastes, and drops suitable for delivery to the eye, ear or nose.

Various alternative pharmaceutical delivery systems may be employed. Non-limiting examples of such systems include liposomes and emulsions. Certain organic solvents such as dimethylsulfoxide also may be employed. Additionally, the compounds may be delivered using a sustained-release system, such as semipermeable matrices of solid polymers containing the therapeutic agent. The various sustained-release materials available are well known by those skilled in the art. Sustained-release capsules may, depending on their chemical nature, release the compounds over a range of several days to several weeks to several months.

Induction of cell differentiation is also stimulated by administering peptide fragments of angiocidin comprising the amino acid sequence of SEQ ID NO:2 or SEQ ID NO:3, and mimetic peptides exhibiting these effects. These therapeutic peptides can be formulated and administered as described above.

The following examples are provided to describe the invention in greater detail. The examples are intended to illustrate, not to limit, the invention.

EXAMPLE 1

Preparation of Recombinant Angiocidin

Purified, recombinant, his-tagged angiocidin was expressed in bacteria and purified as described in Zhou, et al., *J. Cell Biochem.* 92: 125-146, 2004.

EXAMPLE 2

Angiocidin Induces Differentiation of Monocytes to Macrophages

THP-1 cells, a monocytic leukemic human cell line (ATCC No. TIB-202), were cultured and treated with angiocidin or with conditioned medium from monocyte and T-cell cultures as described in Kremlev, et al., *J. Neuroimmunol.* 194: 132-142, 2008 ("Kremlev"). Treatment with 1.0 µg/mL angiocidin for 24 h induced a dramatic morphological change in the THP-1 cells as shown in FIG. 1. Normally, THP-1 cells grow in suspension and do not attach to a culture surface. However, angiocidin-treated cells became adherent, spread on plastic and on matrix proteins, e.g., collagen, and developed focal adhesion contacts containing vinculin (Kremlev).

The ability of angiocidin to induce these phenotypic changes requires the 20 amino acid sequence of SEQ ID NO:2. This 20 amino acid sequence binds to $\alpha 2\beta 1$ integrin (Sabherwal, et al., *Exp. Cell. Res.* 312: 2443-2453, 2006). A deletion mutant of angiocidin lacking this sequence failed to induce morphological changes. However, a 25 amino acid peptide comprising these 20 amino acids was capable of inducing the phenotypic changes observed after treatment with the full angiocidin protein (Kremlev).

Figure 2A:
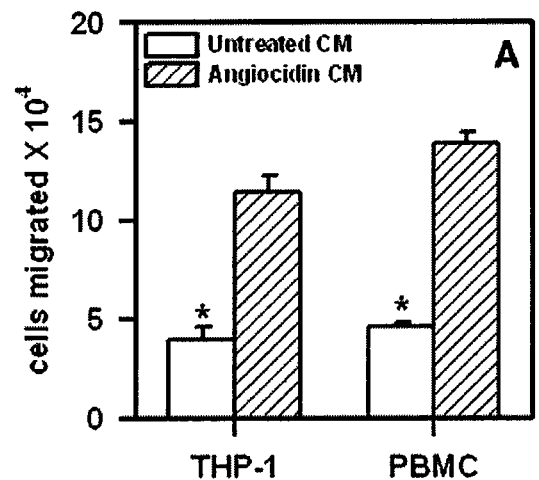
FIG. 2 presents graphs showing the effects of angiocidin-conditioned medium on THP-1 and PBMC cell migration through A—gelatin, B—a HUVEC layer. C shows the effects of a 25 amino acid peptide comprising SEQ ID NO:2 on adhesion of THP-1 cells.
Figure 2B:
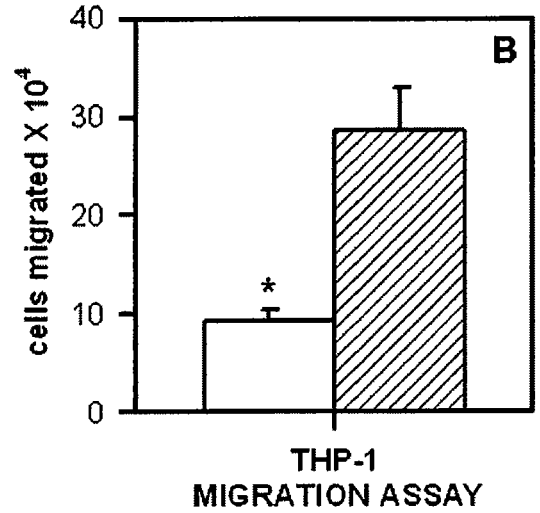
Figure 2C:
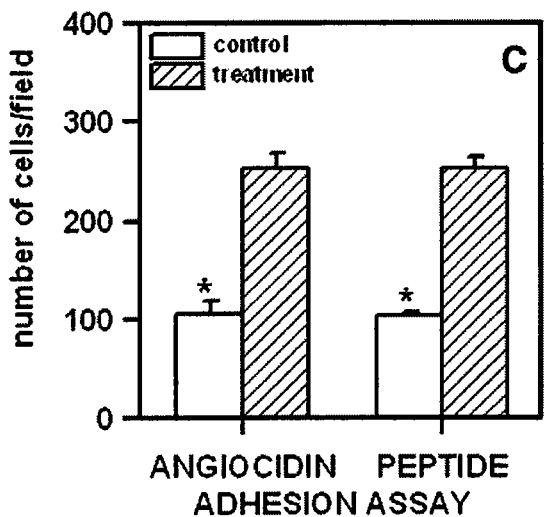

Treatment with conditioned medium from angiocidin-treated THP-1 cell cultures (from which free angiocidin was removed by immunoadsorbtion) also stimulated THP-1 cell adhesion and cell migration as shown in FIG. 2, (methods described in Kremlev), suggesting that angiocidin treatment stimulates the production of factors that induce cell differentiation.

Figures 3A, 3B, 3C, 3D:
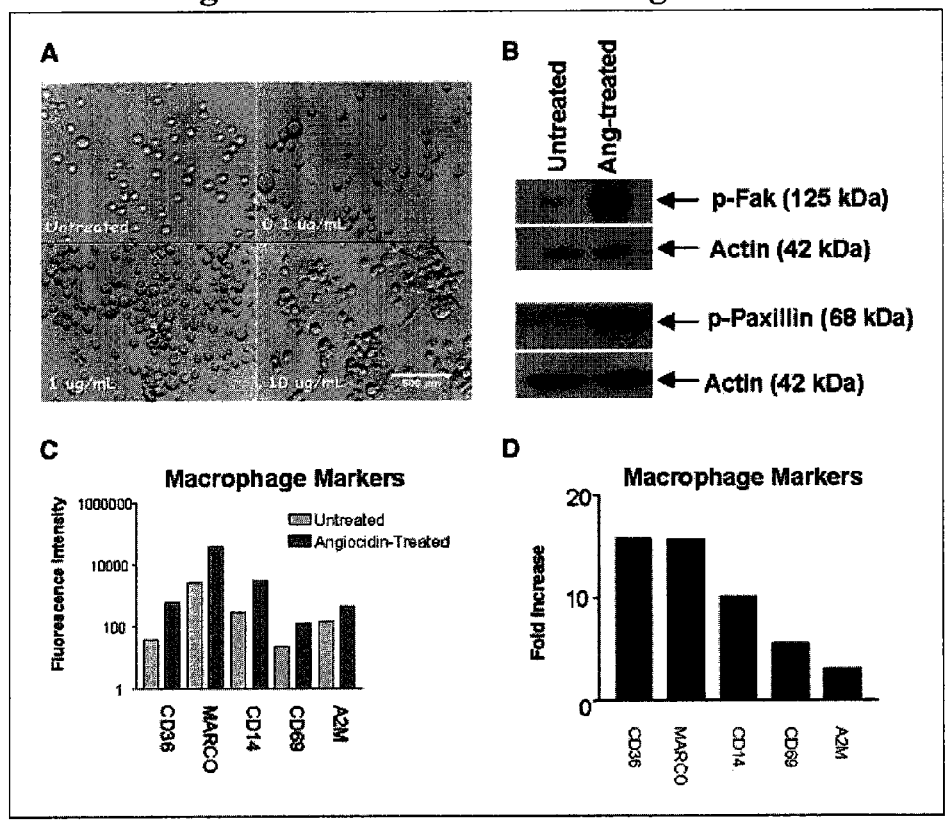
FIG. 3 shows the effects of angiocidin on the morphology and phenotype of THP-1 cells.
Figures 4A, 4B, 4C, 4D:
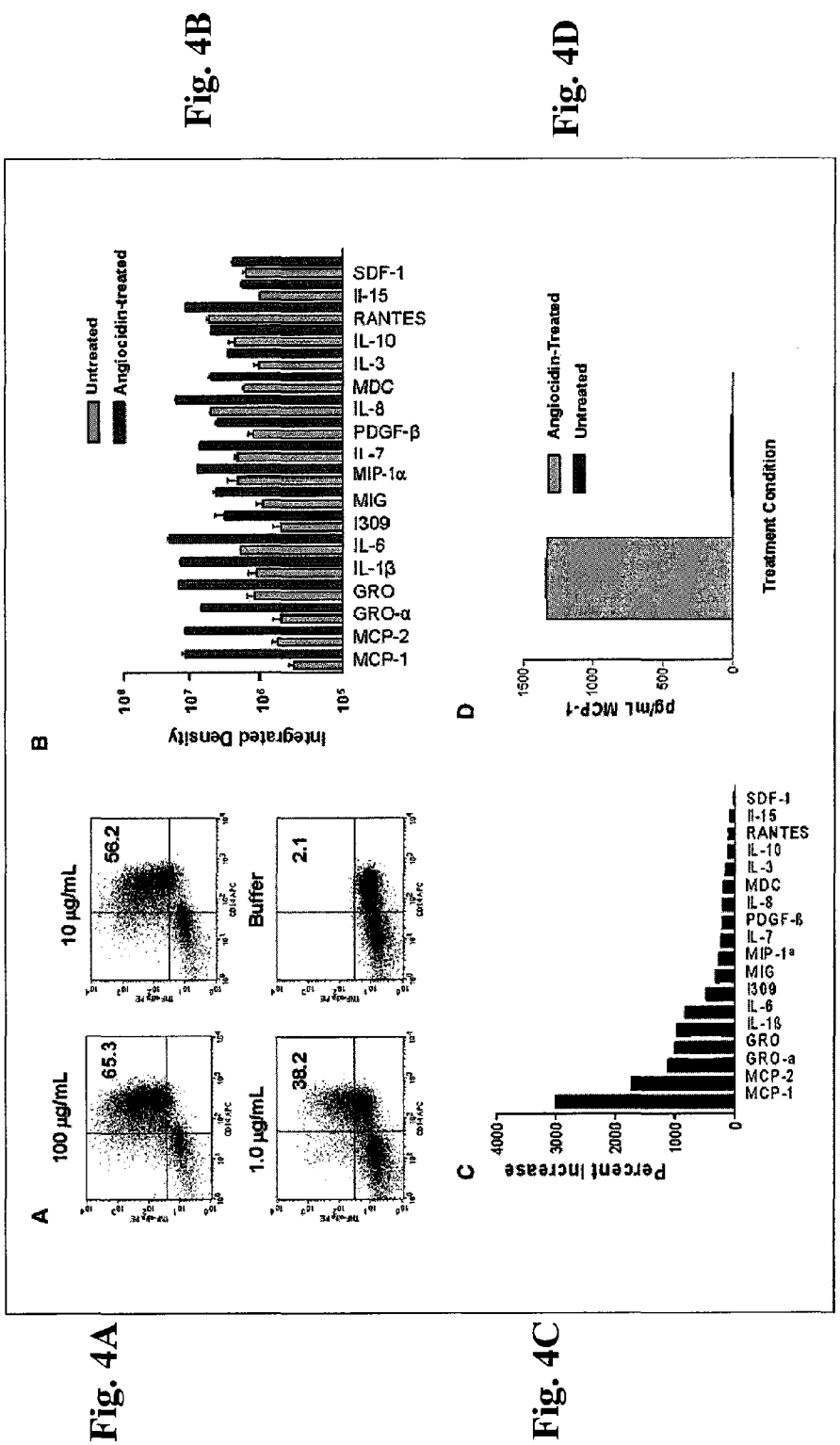
FIG. 4 shows the effects of angiocidin on human PBMC and THP-1 cells. A—Flow cytometric analysis of cellular activation of PBMC. Percentage activation is shown in the upper right quadrant of each plot. B—Integrated density values for inflammatory mediators secreted by THP-1 cells. C—Percentage increase in each cytokine in culture medium following treatment with angiocidin. D—Concentration of MCP-1 in culture medium of THP-1 cells.

Angiocidin-treated THP-1 cells developed focal adhesions and exhibited an increase in phosphorylated FAK protein and phosphorylated paxillin. Angiocidin also stimulated mRNA expression for a number of proteins that are "differentiation state dependent," including CD36, MARCO, CD14, CD69, and $\alpha 2$-macroglobulin (FIG. 3). Angiocidin treatment also increased the concentration of specific inflammatory cytokines and chemokines secreted into the culture medium as shown in FIG. 4. Experimental procedures underlying the results shown in FIGS. 3 and 4 were derived from Gaurnier-Hausser, et al., *Cancer Research* 68: 5905-5914, 2008.

Monocyte to macrophage differentiation is characterized by an increase in phagocytic activity (Reyes, et al., *Infect. Immun.* 67: 3188-3192, 1999). Similarly, angiocidin-treated THP-1 cells acquired increased phagocytic activity upon differentiation. Furthermore, angiocidin treatment stimulated THP-1 cells to secrete active matrix metalloproteinase 9 (MMP-9) in the same manner as activated macrophages. (Gaurnier-Hausser, et al., *Cancer Res.* 68: 5905-5914, 2008).

These results demonstrate that angiocidin can induce differentiation of monocytes in human blood and suggest that angiocidin could be used to inhibit tumor cell proliferation and secondary metastasis and in the treatment of leukemia.

EXAMPLE 3

Immune Stimulation of T-Lymphocytes from Human Blood

Human peripheral blood mononuclear cells (PBMC) were collected, and mononuclear (MNP) and T-cell enriched cell populations were obtained and cultured as described in Kremlev. Cell cultures were treated with angiocidin at 1.0 µg/mL overnight. Conditioned medium from treated cultures was collected and analyzed on a membrane array of cytokines obtained from RayBiotech, Inc. (RAYBIO® Human Cytokine Antibody Array 3) as described in Kremlev. Angiocidin treatment activated CD4+ and CD8+ T-lymphocytes and stimulated the synthesis and secretion of inflammatory cytokines in T-cell and MNP cell populations (Kremlev). These results show that angiocidin is a potent systemic immune stimulator that can induce inflammatory signals in autoimmune diseases, such as multiple sclerosis (MS).

EXAMPLE 4

Angiocidin Facilitates Antigen Presentation by MNP Cells to T-Lymphocytes

Transcription of RNA for proteins important in antigen presentation was increased in THP-1 cells after angiocidin treatment (Kremlev). These proteins included HLA-DPB2, HLA-DPB1, and B7-2. Therefore, the effects of angiocidin on antigen presentation were examined.

Peripheral blood mononuclear cells (PBMC) were plated on tissue culture dishes. The adherent monocyte fraction was treated with 1.0 µg/mL angiocidin for seven days to in the presence or absence of the antigen, human myelin basic protein peptide (MBP) at 40 µg/mL. The non-adherent PMBC fraction, which contained T-cells, was separately treated with angiocidin in the presence and absence of MBP. The culture medium was then removed from the cultured monocytes and the cells were challenged with nonadherent PBMC. Challenging PBMC comprised three groups: untreated (control) cells; MBP-treated cells, and MBP+angiocidin-treated cells. Conditioned medium was collected at 24 and 48 h and analyzed for IL-2 by ELISA. Methods and results are described in detail in Kremlev.

Figure 5A:
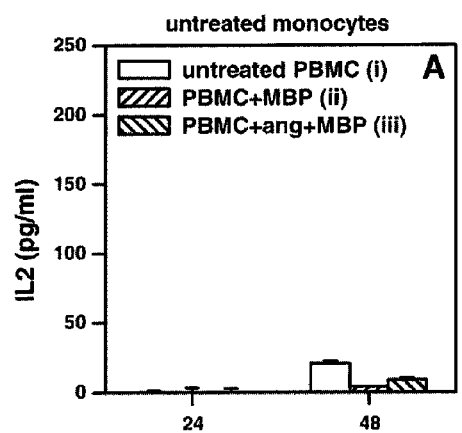
FIG. 5 shows the generation of antigen-specific IL-2 producing cells in angiocidin- and/or MBP-treated monocytes challenged with untreated PBMC or PBMC treated with angiocidin, MBP, or angiocidin+MBP.
Figure 5B:
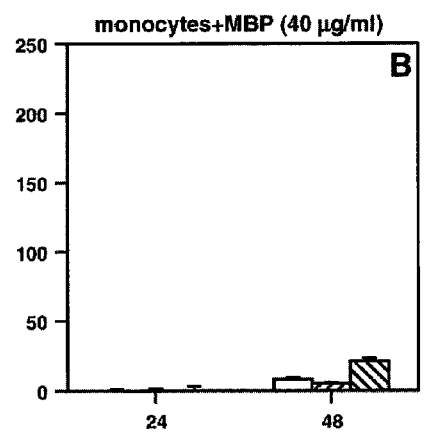
Figure 5C:
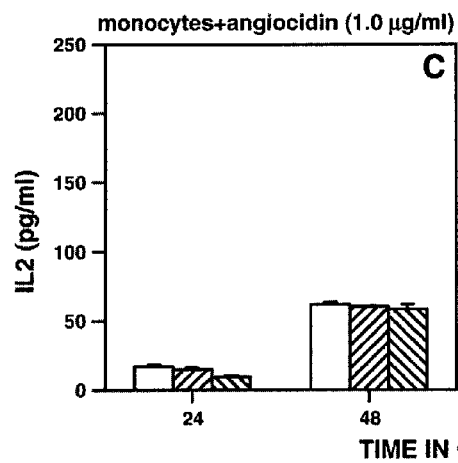
Figure 5D:
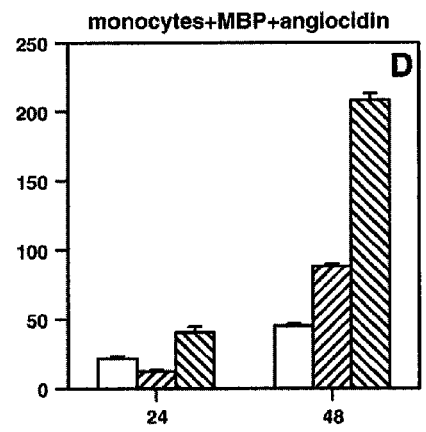

As shown in FIG. 5, a significant increase in IL-2 production was found in angiocidin+MBP treated monocytes challenged by angiocidin+MBP-treated PBMC after 24 and 48 h in culture (FIG. 5D). A significant, but smaller, increase in IL-2 production was also observed in angiocidin+MBP-treated monocytes challenged with MPB-treated PBMC (FIG. 5D).

These results demonstrate that angiocidin promotes antigen presentation and increases the ability of antigen-specific T-effector lymphocytes to produce IL-2, which is a marker for proliferating T-cells presented with antigen (Robb, et al., *J. Exp. Med.* 154: 1455-74, 1981. IL-2 is referred to in this paper as TCGF).

EXAMPLE 5

Angiocidin is Expressed in MS Lesions of MS Patients

Immunohistochemistry was performed on sections of brain from 14 patients with MS as described in Kremlev. Prominent angiocidin expression and IL-7 expression was observed in astrocytes and the surrounding extracellular matrix within demyelinated plaques in all 14 patients as shown in FIG. 1 of Kremlev. Normal tissue in adjacent areas showed no expression of angiocidin. These results, taken with the results from Examples 3 and 4 suggest that angiocidin and its downstream mediators are important target molecules in the treatment of MS.

EXAMPLE 6

Induction of Differentiation of Blastomere-Like Stem Cells from Human Blood

Figure 6A:
FIG. 6 presents phase-contrast micrographs of BLSC from human blood following treatment with A—angiocidin, B—bFGF, or C—bFGF+EGF.
Figure 6B:
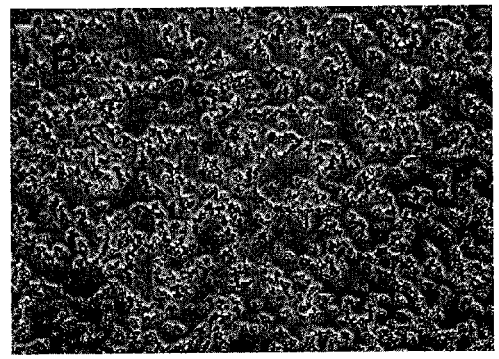
Figure 6C:
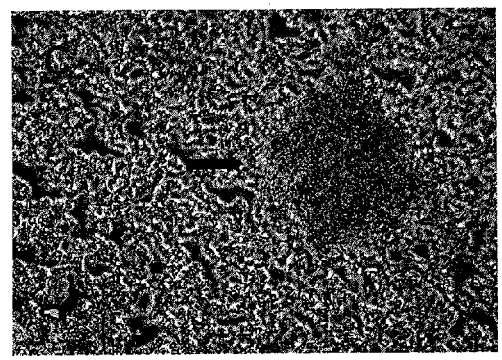

Blastomere-like stem cells (BLSC) (www.moragabiotech.com/techblscs.htm) are small (less than 2 µm diameter) totipotent stem cells that were isolated from human blood and provided by Moraga Biotechnology Corporation. BLSC proliferate as undifferentiated spheroidal cells in suspension when plated on collagen-coated tissue culture dishes. However within 24 h of the addition of 10 µg/mL angiocidin to the medium, most of the cells adhere to collagen in coated tissue culture dishes and show enhanced growth potential as evidenced by the accumulation of large aggregates to (FIG. 6A, arrows). Angiocidin has the ability to induce proliferation in both adherent and non-adherent subpopulations of BLSC. Angiocidin has an equal or greater effect on the adherent subpopulation of BLSC as bFGF and EGF, potent stem cell growth factors, in aggregating BLSC on collagen-coated dishes when added at 20 ng/mL (FIG. 6B). However, the combination of bFGF and angiocidin at 20 ng/mL and 10 µg/mL, respectively, elicits similar effects on BLSC as angiocidin alone (FIG. 6C, arrow).

These results demonstrate that angiocidin has potential in stimulating proliferation of blood-derived stem cells, suggesting that angiocidin could be used as a general inductant in combination with specific stem cell growth factors to produce differentiated cells for cell and tissue regeneration during tissue repair. These results suggest important uses for angiocidin not only in the health care industry, but also in the cosmetic industry.

EXAMPLE 7

Inhibition of Melanoma Stem Cell Proliferation

Figure 7A:
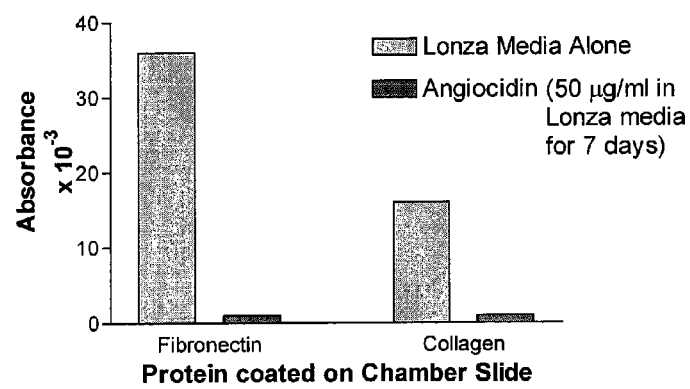
FIG. 7 presents graphs showing the effects of angiocidin on proliferation of melanoma stem cells after A—one week, or B—two weeks.
Figure 7B:
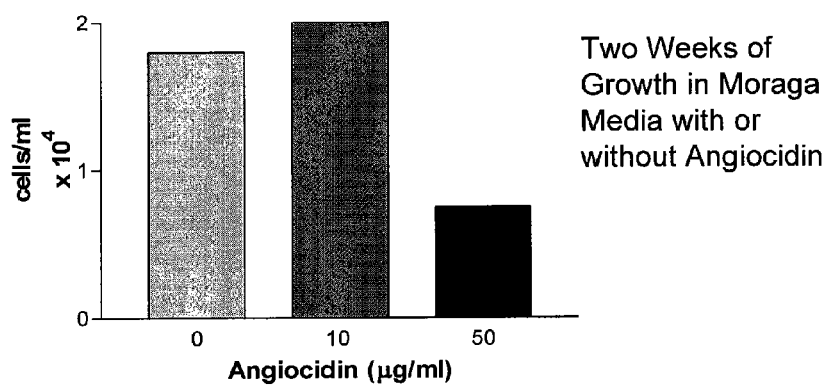

Stem cells capable of developing into melanoma cells were obtained from Dr. Meenhard Herlyn and are described in Fang, et al., *Cancer Research* 65: 9328-9337, 2005. The cells were plated in 8-well chamber slides either uncoated, or coated with 2 µg fibronectin or Type 1 collagen (Fisher Scientific), and grown in mesenchymal stem cell media supplemented with 5 ng/mL fibroblast growth factor (Invitrogen mesenchymal stem cell media or Moraga stem cell media). Type I collagen (1 mg/mL) was dissolved in 0.1N acetic acid and each well was coated with 2 µg of the collagen solution by evaporating 100 µL of a 30% ethanol solution containing 2 µL of the 1 µg/mL stock solution per well of the chamber. After one and two weeks, cell number was assessed colorimetrically using the Almar Blue assay (Biosource). As shown in FIG. 7, 50 µg/mL of angiocidin treatment inhibited cell proliferation by about 60-90%. These results demonstrate that angiocidin is a potent inhibitor of melanoma stem cell proliferation and suggest that angiocidin would be an effective therapy for inhibiting melanoma.

EXAMPLE 8

Angiocidin Promotes Neurite Outgrowth

PC12 is a cell line derived from a pheochromocytoma of the rat adrenal medulla (Greene La., Tischler A S (July 1976). "Establishment of a noradrenergic clonal line of rat adrenal pheochromocytoma cells which respond to nerve growth factor". *Proc. Natl. Acad. Sci. U.S.A.* 73 (7): 2424-8.). PC12 cells stop dividing and terminally differentiate when treated with nerve growth factor (NGF). This makes PC12 cells useful as a model system for neuronal differentiation. It was observed that angiocidin promotes NGF-mediated differentiation of PC12 cells (FIG. 8).

Figure 8A:
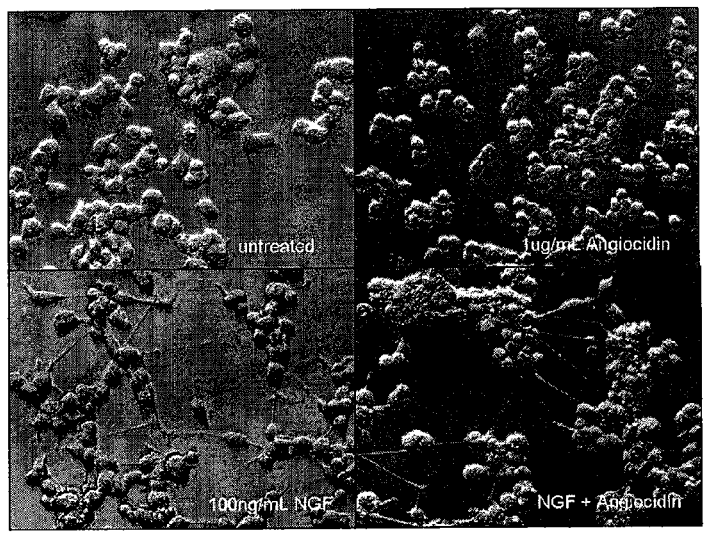
FIG. 8 shows the effect of angiocidin on PC12 neurite growth.
Figure 8B:
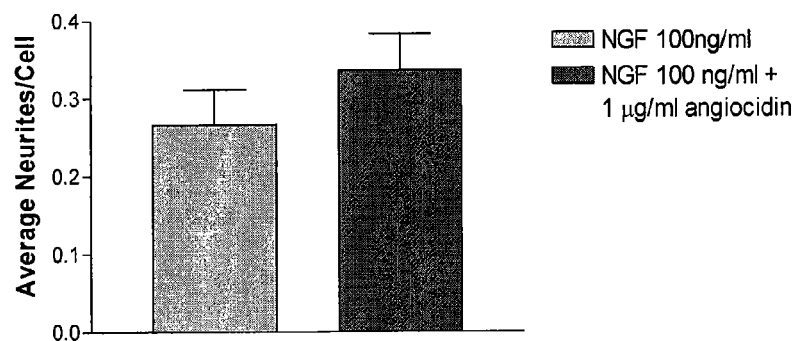

FIG. 8 shows the effect of angiocidin on PC12 neurite outgrowth. Briefly, PC-12 cells were plated in six well plates at a density of $2.5 \times 10^5$ cells/mL in 1 mL of Dulbecco's Modified Eagle Medium (DMEM) containing 1% horse serum and 1% Penicillin and streptomycin, treated with 100 ng/mL of NGF, 1 µg/mL of recombinant angiocidin, or both and allowed to incubate at 37° for 72 hours. After 72 hours, pictures were taken of five random fields at 400× using Hoffman lens. Neurite outgrowth was quantitated using Image 3 software, a public source open access program. To be considered a neurite, a process had to meet the following criteria: (1) Neurite had to be at least 10 µm in length; (2) Neurite had to start and end within the field of vision; and (3) Neurites with branches were measured to the branching point and then each branch was measured separately.

EXAMPLE 9

Angiocidin Inhibits Glioma Stem Cell Growth

Figure 9:
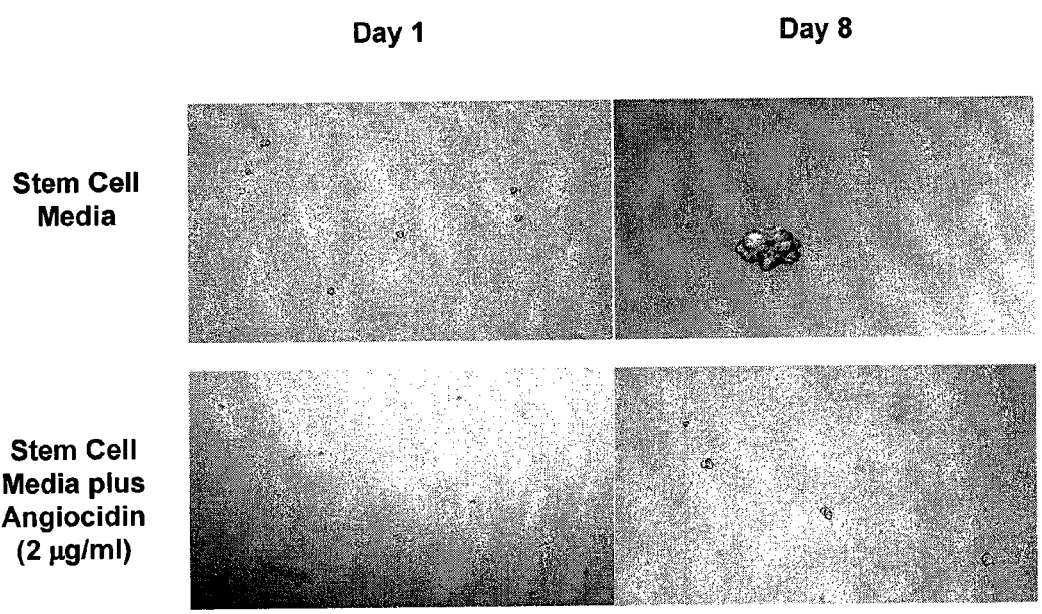
FIG. 9 shows the effect of angiocidin on the growth of glioma stem cells.

FIG. 9 shows the effect of angiocidin on growth of glioma stem cells. This figure shows that when glioma stem cells are cultured for eight days in stem cell media consisting of Dulbecco's Modified Eagle's Medium/Nutrient F-12 Ham containing 100 ng/ml basic fibroblast growth factor, they self-renew forming a multicellular spheroidal cell mass containing approximately 50-100 stem cells. However, when these cells were cultured in stem cell media containing 2 μg/ml angiocidin, proliferation was completely inhibited and eventually the cells died.

Cells were viewed under phase contrast microscopy at 200× magnification. Briefly, glioma stem cells were isolated from a resected tumor obtained from a patient with glioma multiforma (GBM). Tumor tissue was dissociated in phosphate buffered saline by treatment of minced tumor tissue with collagenase (1 mg/ml) for one hour. Cells were harvested by centrifugation and the cells plated in stem cell media in a six well plate coated with mouse anti-CD33 IgG (coated by incubating the plates with 1 μg/ml anti-CD33 IgG overnight followed by one rinse in phosphate buffered saline containing 1 mg/ml bovine serum albumin). After one hour incubation, adherent cells were removed by scraping and 50 cells were plated into six well culture dishes in stem cell media with and without 2 μg/ml angiocidin. Growth of cells was monitored for eight days. FIG. 9 shows a representative high power field from untreated and angiocidin-treated cells.

EXAMPLE 10

Angiocidin Binds Basic Fibroblast Growth Factor (FGF-2) and Nerve Growth Factor (NGF)

Figure 10A:
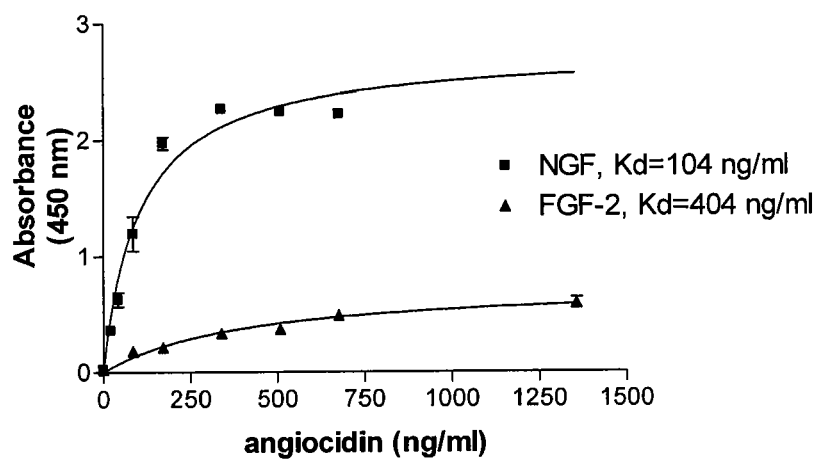
FIG. 10 shows direct binding of angiocidin to adsorbed nerve growth factor (NGF) and fibroblast growth factor-2 (FGF-2).

Since neurite outgrowth and stem cell renewal is dependent on growth factors such as NGF and FGF-2, whether angiocidin binds to these growth factors was investigated. A simple binding assay was developed, in which the growth factors are adsorbed to the wells of a micotiter dish and the adsorbed factors are allowed to bind with biotinylated angiocidin. The bound biotinylated angiocidin was detected with streptavidin-coupled horse radish peroxidase and developed with the colorimetric substrate ultra 3,3',5,5'-tetramethylbenzidine (TMB) (FIG. 10A). To determine that biotinylated angiocidin binds specifically, we were able to show that binding was competed with unbiotinylated angiocidin (FIG. 10B).

Figure 10B:
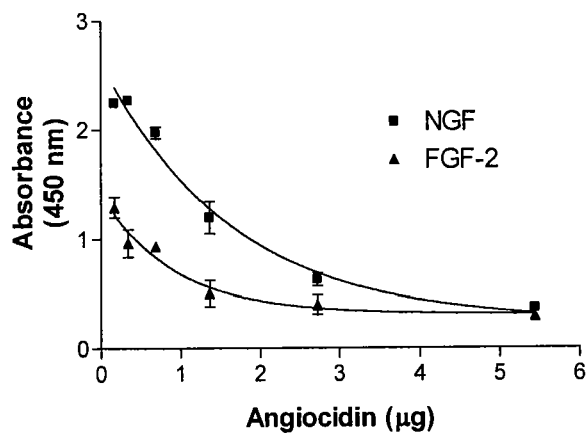

As shown in FIG. 10, angiocidin directly binds to adsorbed NGF and FGF-2. Briefly, in a 96-well plate, 1 ng of NGF or FGF-2 in a 20 mM HEPES buffer was adsorbed to the well in duplicate overnight at 4° C. Remaining buffer was aspirated and the wells were washed with phosphate-buffered saline (PBS). Then, the plate was blocked in 1% (w/v) BSA in PBS for 30 minutes without shaking. Aliquots in a 20 mM HEPES buffer containing various dilutions of biotinylated angiocidin prepared according to Sabherwal Y., Rothman, V. L., Svetoslav, D, L'Heureax D. Z., Marcinkiewicz, C., Sharma, M., and Tuszynski, G. P., Integrin α2β1 mediates the anti-angiogenic and anti-tumor activities of angiocidin, a novel tumor-associated protein, Experimental Cell Research, 312: 2443-2453, 2006 were added to the wells. The 96 well plate was incubated at room temperature with shaking for two hours. Remaining protein solutions were aspirated and then the plate was washed with tris-buffered saline containing 0.1% Tween 20 (TBST) three times. An aliquot of 100 μl of a 0.05 μg/ml streptavidin horseradish peroxidase solution dilution in TBST was added for 30 minutes with shaking. Remaining reagent was then aspirated and the wells were washed three times with TBST. Ultra 3,3',5,5'-tetramethylbenzidine (TMB) was added in each well for 15 minutes and 100 μl of 0.5M $H_2SO_4$ was added to stop the reaction and the plate read in an ELISA plate reader at 450 nm. For competition experiments shown in FIG. 10B, non-biotinylated protein was added to 100 ng/ml biotinylated angiocidin and binding was performed in either FGF-2 or NGF-coated plates as described above.

EXAMPLE 11

Figure 11:
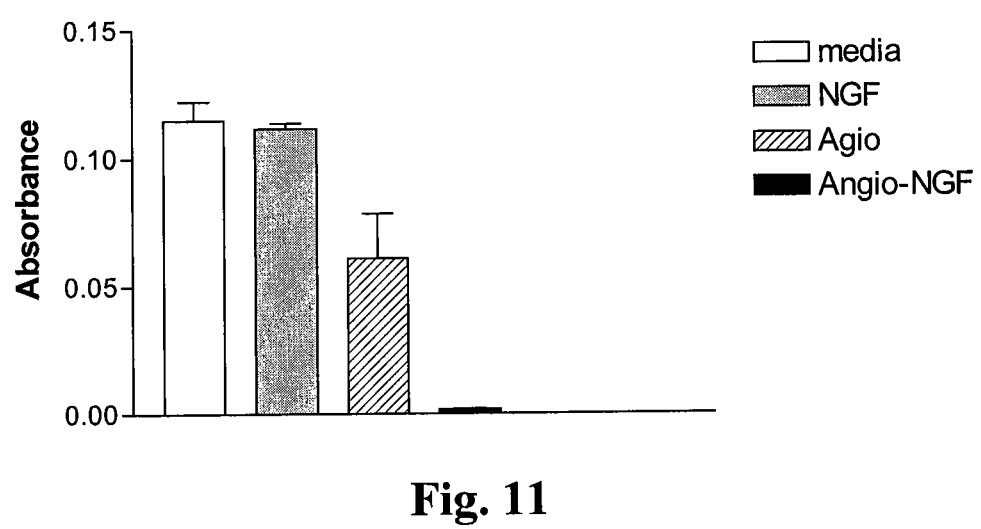
FIG. 11 shows the effect of angiocidin and NGF on MDA MB231 breast carcinoma proliferation.

Angiocidin and NGF Induce Cell Arrest and Apoptosis in MDA MB231 Breast Carcinoma Cells To determine if angiocidin growth factor complex plays any role tumor cell proliferation, breast cancer cells, which are known to possess receptors for NGF were treated for 48 hours with either serum-free media containing 1 mg/ml BSA, or media-free media containing 1 mg/ml BSA with either 10 μg/ml of angiocidin, 10 μg/ml angiocidin plus 100 ng/ml NGF, or 100 ng/ml NGF. Total viable cells were then determined using the Almar blue assay as previously described in Sabherwal Y., Rothman, V. L., Svetoslav, D, L'Heureax D. Z., Marcinkiewicz, C., Sharma, M., and Tuszynski, G. P., Integrin α2β1 mediates the anti-angiogenic and anti-tumor activities of angiocidin, a novel tumor-associated protein, Experimental Cell Research, 312: 2443-2453, 2006. The data in FIG. 11 show that NGF and angiocidin induce growth arrest and cell death after 48 hours.

These data show that angiocidin in the presence of NGF promotes differentiation of PC12 cells and induces cell death of breast cancer cells. Additionally, angiocidin causes growth arrest of glioma stem cells presumably by its ability to complex FGF-2. Since angiocidin binds NGF and FGF-2, we propose that angiocidin-growth factor complex inhibits stem cell growth by withdrawing growth factor from the cells while angiocidin NGF complexes promote cell differentiation while promoting tumor cell growth arrest and apoptosis.

EXAMPLE 12

Effect of Angiocidin on Growth of Human Breast Tumors

In FIG. 12, the data show that MDA-MB-231 human breast tumor cells transfected with angiocidin to over-express angiocidin formed smaller colonies in soft agar and developed smaller tumors when injected subcutaneously into athymic mice.

EXAMPLE 13

Angiocidin-Transfected MDA-MB-231 Tumor Cells Develop Smaller Tumors in Mice and Smaller Colonies in Soft Agar MDA-MB-231 breast cancer cells were transfected with angiocidin using the pcDNA3.1 transfection system as described by the manufacturer. At least two angiocidin over-expressing clones were selected: sense 1 and 2, as well as the vector control. In FIG. 12, the panels marked sense show the sense 1 clone. Similar results were obtained with sense 2 clones. Panel A shows paraformaldehyde-fixed cells grown in culture and stained with anti-angiocidin antibody and developed with DAB (100×). Panel B shows Western blot of cells grown in panel A. Panel C shows colonies grown in soft agar as seen by phase contrast phase contrast (50× mag). Panel D shows tumor volumes of cells grown in mice (n=6 per group±std). Athymic mice were injected with 1 million cells subcutaneously and tumors allowed to develop for three weeks. Tumor volumes were measured as previously described (J. Zhou, V. L. Rothman, I. Is Sargiannidou, S. Dimitrov, C. Qiu, E. Smith, J. Sheffield, M. Sharma, G. P. Tuszynski, Cloning and characterization of angiocidin, a tumor cell binding protein for thrombospondin-1, 3 Cell Biochem 92 (2004) 125-146).

EXAMPLE 14

The Effect of Angiocidin on Differentiation of Leukemia Stem Cells

Figure 13:
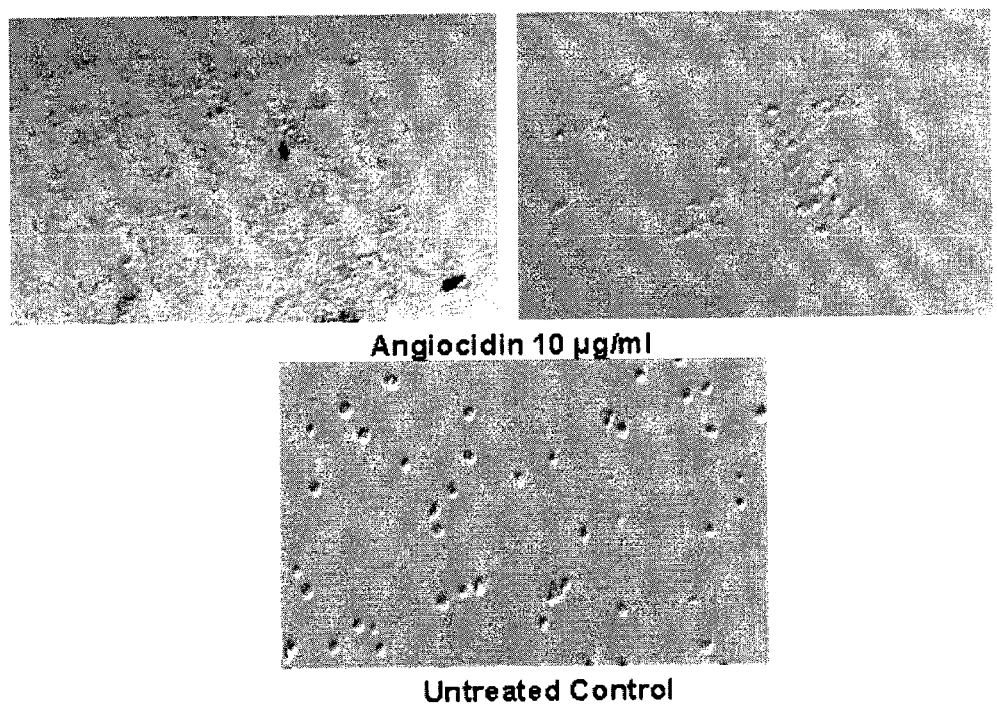
FIG. 13 shows that angiocidin differentiates CD34+CD38- Leukemic stem cells. Cells were photographed at 200× magnification using Hoffman interference microscopy.

The CD34+/CD38− stem cell subset of the AML cell line THP-1 was recently isolated by magnetic bead cell sorting. These cells were cultured in serum-free media in the absence and presence of 10 μg/ml of angiocidin for 48 hours. Cells in the absence of angiocidin remained rounded while those in the presence of angiocidin all became adherent and spread (FIG. 13). The angiocidin-differentiated cells were morphologically indistinguishable from the parental mixed population that was differentiated by angiocidin. These results strongly suggest that angiocidin may be targeting the leukemic stem cell population and further underscore the high clinical impact of angiocidin as a potential therapeutic for the treatment of leukemia.

The present invention is not limited to the embodiments described and exemplified above, but is capable of variation and modification within the scope of the appended claims.

What is claimed:

1. A method of treating a leukemia in a subject, comprising administering to the subject an amount of angiocidin effective to treat the leukemia.

2. The method of claim 1, wherein angiocidin is administered in a composition comprising angiocidin and a pharmaceutically acceptable carrier.

3. The method of claim 2, wherein angiocidin is administered to the subject in a dose of about 0.001 to 10 mg/kg body weight.

4. The method of claim 1, wherein the treatment induces differentiation of the subject's leukemia cells when said leukemia cells contact angiocidin.

5. The method of claim 4, wherein the differentiation inhibits the tumorigenicity of the subject's leukemia cells when said leukemia cells contact angiocidin.

6. The method of claim 4, wherein the differentiation confers on the subject's leukemia cells a non-cancerous phenotype when said leukemia cells contact angiocidin.

7. The method of claim 4, wherein the status of the treatment of a leukemia is assessed by determining the differentiation of the subject's leukemia cells.

8. The method of claim 5, wherein the status of the treatment of a leukemia is assessed by determining the tumorigenicity of the subject's leukemia cells.

9. The method of claim 6, wherein the status of the treatment of a leukemia is assessed by determining whether the subject's leukemia cells have a non-cancerous phenotype.

10. The method of claim 4, wherein the extent of differentiation of the subject's leukemia cells is determined by measuring monocyte count, macrophage count, T-cell activation, matrix metalloproteinase 9, phosphorylated FAK protein, phosphorylated paxillin, macrophage cell surface markers including CD36, MARC0, CD14, CD69 and a2-macroglobulin, or cytokines and chemokines including MCP-1, MCP-2, GRO-α, GRO, IL-1β, IL-6, 1309, MIG, MIP-1α, IL-7, PDGG-β, IL-8, MDC, IL-3, IL-10, RANTES, IL-15 and SDF-1.

11. The method of claim 4, wherein the extent of differentiation of the subject's leukemia cells is determined by assessing morphology, adherence to plastic, spreading on plastic or matrix proteins including collagen, development of focal adhesion contacts, cell migration, or phagocytosis.

12. The method of claim 5, wherein the tumorigenicity of the subject's leukemia cells is determined by measuring proliferation, growth in soft agar, invasion, phagocytosis, or anchorage dependent growth.

13. The method of claim 6, wherein the presence of a non-cancerous phenotype is determined by measuring proliferation, growth in soft agar, invasion, phagocytosis, or anchorage dependent growth.

\* \* \* \* \*

UNITED STATES PATENT AND TRADEMARK OFFICE
CERTIFICATE OF CORRECTION

Page 1 of 1

PATENT NO. : 8,901,083 B2
APPLICATION NO. : 13/130898
DATED : December 2, 2014
INVENTOR(S) : George P. Tuszynski It is certified that error appears in the above-identified patent and that said Letters Patent is hereby corrected as shown below:

In the Specification

On Column 1, Line 15, please replace the paragraph titled "STATEMENT REGARDING FEDERALLY SPONSORED RESEARCH" with the following paragraph:
-- STATEMENT REGARDING FEDERALLY SPONSORED RESEARCH
This invention was made with government support under R01 CA088931 awarded by the National Institutes of Health. The government has certain rights in the invention. --

Signed and Sealed this
Seventh Day of November, 2023

Katherine Kelly Vidal
*Director of the United States Patent and Trademark Office*